(12) United States Patent
Kerkhoffs et al.

(10) Patent No.: US 10,213,536 B2
(45) Date of Patent: Feb. 26, 2019

(54) IMPLANTABLE CONNECTOR ASSEMBLY AND METHOD OF COMMUNICATING AN ELEMENT TO AN IMPLANTABLE DEVICE

(71) Applicant: CircuLite, Inc., Teaneck, NJ (US)

(72) Inventors: Wolfgang Kerkhoffs, Aachen (DE); Ellen Keysselitz, Aachen (DE); J. Christopher Flaherty, Auburndale, FL (US); Josef Weigand, Heldenstein (DE)

(73) Assignee: CircuLite, Inc., Teaneck, NJ (US)

( * ) Notice: Subject to any disclaimer, the term of this patent is extended or adjusted under 35 U.S.C. 154(b) by 379 days.

(21) Appl. No.: 14/432,548

(22) PCT Filed: Sep. 30, 2013

(86) PCT No.: PCT/US2013/062607
§ 371 (c)(1),
(2) Date: Mar. 31, 2015

(87) PCT Pub. No.: WO2014/055407
PCT Pub. Date: Apr. 10, 2014

(65) Prior Publication Data
US 2015/0250933 A1 Sep. 10, 2015

Related U.S. Application Data

(60) Provisional application No. 61/809,984, filed on Apr. 9, 2013, provisional application No. 61/744,694, filed on Oct. 2, 2012.

(30) Foreign Application Priority Data

Oct. 1, 2012 (DE) .................... 10 2012 019 219

(51) Int. Cl.
*A61M 1/10* (2006.01)
*A61N 1/372* (2006.01)
(Continued)

(52) U.S. Cl.
CPC .......... *A61M 1/1008* (2014.02); *A61M 39/10* (2013.01); *A61M 39/16* (2013.01);
(Continued)

(58) Field of Classification Search
CPC ........................... A61M 1/101; A61M 25/04
See application file for complete search history.

(56) References Cited

U.S. PATENT DOCUMENTS 4,445,511 A * 5/1984 Cowdery ............. A61N 1/3752
607/37
5,749,909 A * 5/1998 Schroeppel .......... A61N 1/3787
607/33
(Continued)

FOREIGN PATENT DOCUMENTS

EP 1386634 A1 2/2004
JP 49-137084 11/1974
(Continued)

OTHER PUBLICATIONS

Chinese Patent Office, Office Action in CN Application No. 201380061348.5, dated May 4, 2016.
(Continued)

*Primary Examiner* — Michael D Abreu
(74) *Attorney, Agent, or Firm* — Christopher & Weisberg, P.A.

(57) ABSTRACT

An implantable connector assembly (14) for communicating an element to an implantable device (12) within a patient (20) comprises a plug (16), a receptacle (18), and a pair of communication structures (72, 108). The plug (16) includes a plunger body (64). The receptacle (18) includes a sleeve (98) and a stopper (114). The sleeve (98) defines an opening (104), and the stopper (114) is resiliently mounted within the sleeve (98) to cover and fluidly seal the opening (104). The pair of communication structures (72, 108) is positioned
(Continued)

respectively on the plunger body (64) and the sleeve (98). One of the communication structures (72, 108) connects to a source and the other communication structure (108, 72) connects to the implantable device (12). The plunger body (64) inserts into the sleeve (98) to displace the stopper (114) and couple the pair of communication structures (72, 108) for communication of the element therebetween.

29 Claims, 5 Drawing Sheets

(51) Int. Cl.
    *A61M 39/10*     (2006.01)
    *A61M 39/16*     (2006.01)
    *A61M 39/26*     (2006.01)
    *A61M 1/12*     (2006.01)

(52) U.S. Cl.
    CPC ............. *A61M 39/26* (2013.01); *A61N 1/372* (2013.01); *A61M 1/12* (2013.01); *A61M 1/122* (2014.02); *A61M 1/127* (2013.01); *A61M 2039/1022* (2013.01); *A61M 2039/1044* (2013.01); *A61M 2207/00* (2013.01)

(56) References Cited

U.S. PATENT DOCUMENTS

| | | |
|---|---|---|
| 5,806,551 A | 9/1998 | Meloul et al. |
| 2003/0032940 A1 | 2/2003 | Doyle |
| 2009/0112050 A1* | 4/2009 | Farnan ................ A61M 1/3653 600/16 |
| 2010/0035453 A1* | 2/2010 | Tronnes ............... A61N 1/3752 439/271 |
| 2010/0292674 A1 | 11/2010 | Jepson et al. |
| 2011/0184479 A1 | 7/2011 | Kast et al. |
| 2011/0200451 A1 | 8/2011 | Lehmann et al. |
| 2012/0116470 A9 | 5/2012 | Kast et al. |
| 2012/0178985 A1* | 7/2012 | Walters ............... A61M 1/1024 600/16 |
| 2012/0286185 A1 | 11/2012 | Spolski |

FOREIGN PATENT DOCUMENTS

| | | |
|---|---|---|
| JP | 200465966 A | 3/2004 |
| JP | 2005514181 A | 5/2005 |
| JP | 2012176265 A | 9/2012 |
| WO | 9826835 A1 | 6/1998 |
| WO | 0059561 A1 | 10/2000 |
| WO | 03059439 A2 | 7/2003 |
| WO | 2007025326 A1 | 3/2007 |
| WO | 2006078355 A1 | 7/2016 |

OTHER PUBLICATIONS

U.S. Patent and Trademark Office, International Search Report and Written Opinion in PCT Application Serial PCT/US2013/062607, dated Jan. 3, 2014.

Australian Patent Office, Examination Report No. 1 in Australian Application No. 2013327630, dated Feb. 9, 2017.

European Patent Office, Supplementary Search Report in EP Applicatio No. 13844497.1, dated Dec. 23, 2016.

Japanese Patent Office, Notice of Reasons for Rejection in JP Application No. 2015-535715, dated Aug. 14, 2017.

* cited by examiner

IMPLANTABLE CONNECTOR ASSEMBLY AND METHOD OF COMMUNICATING AN ELEMENT TO AN IMPLANTABLE DEVICE

CROSS-REFERENCE TO RELATED APPLICATION

The application claims priority to German Provisional Application Serial No. 10 2012 019 219.3, filed Oct. 1, 2012 (pending), U.S. Provisional Application Ser. No. 61/744,694, filed Oct. 2, 2012, and U.S. Provisional Application Ser. No. 61/809,984, filed Apr. 9, 2013, the disclosures of which are hereby incorporated by reference herein.

TECHNICAL FIELD

The present invention relates generally to an apparatus and method for communicating an element from a source to an implantable medical device within the patient.

BACKGROUND

Implantable medical devices, such as heart pumps, pacemakers, controllers, batteries, catheters, or drug delivery pumps are well known in the medical arts to improve patient outcomes. These implantable medical devices are surgically positioned within the patient's body and may reside in a subcutaneous pocket during the life of the patient or useful life of the device. During this time, it may be necessary to provide an element, such as an electrical power or medical fluid, to the device within the subcutaneous pocket from a supply source exterior of the patient. For this reason, a cable for communicating these elements connects to the device, extends through the subcutaneous pocket, and terminates outside of the patient for accessing the device.

Traditionally, the connection between the cable and the device is permanently and fluidly sealed to inhibit contaminants from entering the device or cable during use. Such contamination may result from bodily fluids or any foreign matter used during surgery and cause reduced performance or failure of the device. While generally effective at inhibiting harmful contamination during use, the cable extending from the implantable device during surgery tends to block access to the patient. Moreover, depending on the position of the subcutaneous pocket, positioning the implantable device within the pocket may be relatively complex since a surgeon must handle both the implantable device and the cable.

There is a need for an apparatus and method that effectively communicates an element from a source to an implantable medical device while addressing issues such as those discussed above.

SUMMARY

An exemplary embodiment of an apparatus for implantation within a patient comprises an implantable device, a cable, and an implantable connector assembly. The implantable device is configured for being positioned and operating at least subcutaneously within the patient. The cable is configured for communicating an element from a source exterior of a patient or implanted within the patient toward the implantable device within the patient. The implantable connecting assembly includes a plug, a receptacle, and a pair of communication structures. The plug is operatively connected to one of the cable and the implantable device and includes a plunger body. The receptacle is operatively connected to the other of the cable and the implantable device. The receptacle includes a sleeve and a stopper. The sleeve defines an opening sized for receiving the plunger body. The stopper is resiliently mounted within the sleeve and biased toward the opening to cover and fluidly seal the opening for inhibiting contamination from entering within the sleeve when the plunger body is withdrawn from the sleeve. The pair of communication structures is positioned respectively on the plunger body and the sleeve. One of the pair of communication structures operatively connects to the cable for receiving the element from the cable. The other of the pair of communication structures operatively connects to the implantable device for directing the element to the implantable device. Accordingly, the plunger body inserts into the sleeve to displace the stopper and removably couple the pair of communication structures for communication of the element therebetween.

An exemplary embodiment of an implantable connector assembly for communicating an element from a source exterior of a patient or implanted within the patient to an implantable device within the patient comprises a plug, a receptacle, and a pair of communication structures. The plug is configured to operatively connect to one of the source and the implantable device and includes a plunger body. The receptacle is configured to operatively connect to the other of the source and the implantable device and includes a sleeve and a stopper. The sleeve defines an opening sized for receiving the plunger body. The stopper is resiliently mounted within the sleeve and biased toward the opening to cover and fluidly seal the opening for inhibiting contamination from entering the sleeve when the plunger body is withdrawn from the sleeve. The pair of communication structures is positioned respectively on the plunger body and the sleeve. One of the pair of communication structures is configured to operatively connect to the source for receiving the element from the source, and the other of the pair of communication structures is configured to operatively connect to the implantable device for directing the element to the implantable device. Accordingly, the plunger body inserts into the sleeve to displace the stopper and removably couple the pair of communication structures for communication of the element therebetween.

In use, the implantable connector assembly communicates an element from a source to an implantable device within the patient by inserting a plunger body of a plug into a sleeve of a receptacle. The method includes displacing a stopper with the plunger body to unseal an opening in the sleeve. Furthermore, the method includes connecting a communication structure of the plunger body with a communication structure of the sleeve through the opening. The method also includes fluidly sealing the plug against the receptacle to inhibit contamination of the communication structures.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
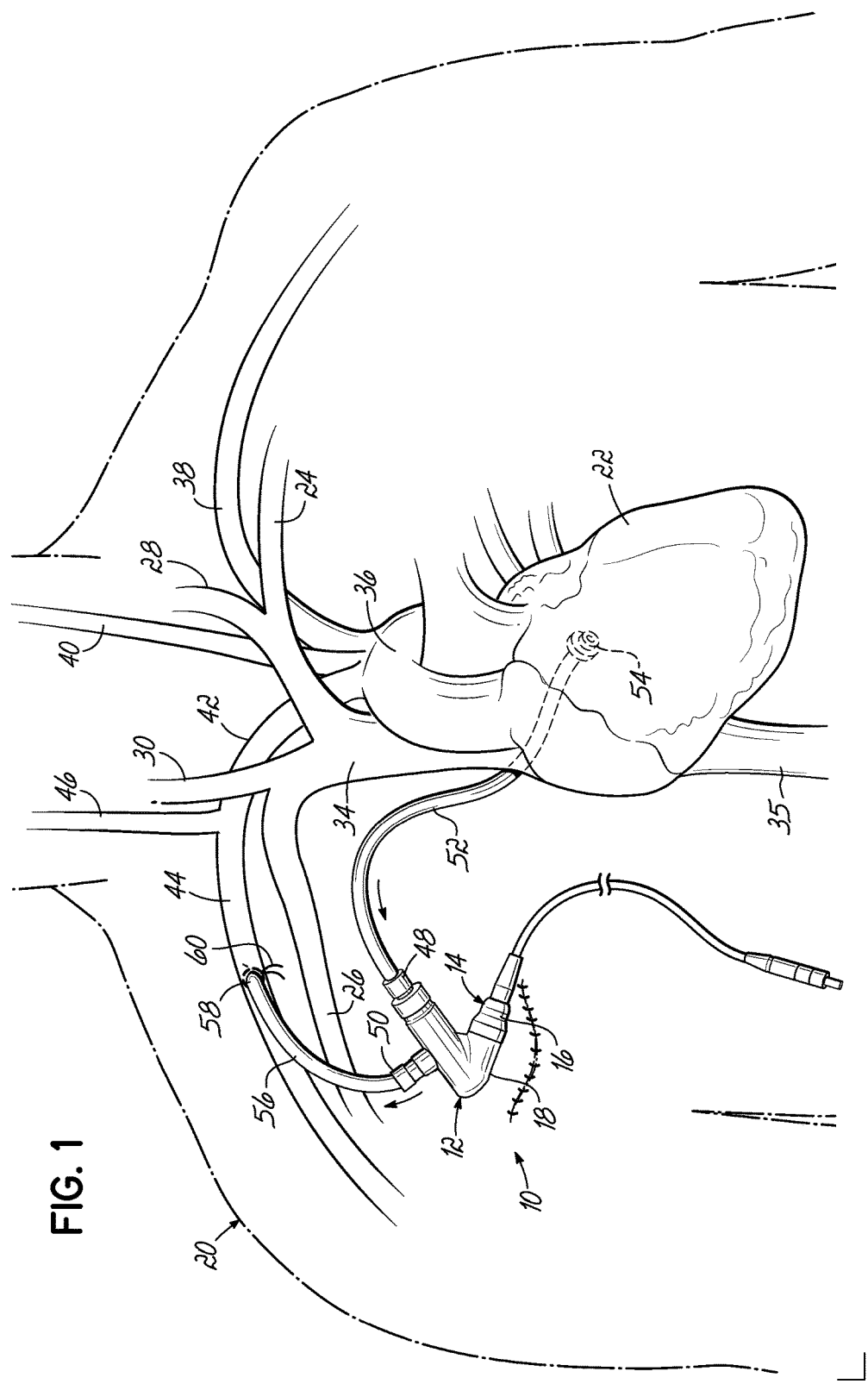
FIG. 1 is a diagrammatic view a circulatory assist system having an apparatus with an embodiment of an implantable connector assembly removably coupled within a patient.

FIG. 1 illustrates an implanted circulatory assist system 10 having an implantable device 12, such as a pump, with an exemplary embodiment of an implantable connector assembly 14. The implantable connector assembly 14 includes a plug 16 cooperating with a receptacle 18 that reduces contamination resulting from removable connection within a patient 20. As used herein, the term "contamination" refers to any bodily fluids or foreign matter that may reduce or destroy communication of an element from the plug 16 to the receptacle 18 if introduced within the implantable connector assembly 14. For illustrative purposes, certain anatomy is shown including a heart 22 of the patient 20 aided by the pump. However, any implantable device 12 may be positioned at least subcutaneously within the patient 20 and include the implantable connector assembly 14 to operatively connect the implantable device 12 to a source, such as a supply source (not shown) exterior of the patient 20 or another implantable device 12 within the patient 20. For example, the implantable device 12 may be in the form of the pump shown in FIG. 1 or, alternatively, may be any other implantable medical device including, but not limited to, a pacemaker, a controller, a battery, a catheter, or a drug delivery pump and operate generally as understood in the current state of the art. While these alternative implantable devices 12 may be positioned elsewhere within the body and configured for alternative operations, it will be appreciated that the implantable connector assembly 14 may be similarly used for communicating one or more elements from exterior of the patient 20 to any implantable device 12 within the patient 20 or between a plurality of implantable devices 12 within the patient 20. As used herein, the term "element" generally refers to any one of an electrical signal, a packet of information, electrical power, and a fluid, such as a liquid or a gas, that may be communicated to the implantable device 12 via the implantable connector assembly 14. Accordingly, the term "element" is not intended to limit the invention to any particular type of communicant passing through the implantable connector assembly 14.

With respect to the implanted circulatory assist system 10 for the heart 22 shown in FIG. 1, blood from an upper portion of the patient 20 moves through the left and right subclavian veins 24, 26 and the left and right jugular veins 28, 30 to enter the superior vena cava 34 and into the heart 22 while blood from a lower portion of the patient 20 enters the heart 22 through the inferior vena cava 35. The blood is pumped to the lungs (not shown) from the right side of the heart 22 to be oxygenated. Blood returning from the lungs reenters the left side of the heart 22 and is then pumped out of the heart 22 and to the aorta 36. From the aorta 36, blood flows in the left subclavian artery 38, the left common carotid 40, and the brachiocephalic trunk 42 including the right subclavian artery 44, the right common carotid 46, and other arterial locations.

The implantable device 12 in the form of the pump includes an input port 48 and an output port 50. An inflow cannula 52 extends from the input port 48 and into a source of oxygenated blood, such as the left atrium (not shown) of the heart 22. An outflow cannula 56 extends from the output port 50 and into an arterial access site 58, shown here to be the right subclavian artery 44. The inflow and outflow cannulae 52, 56 are held in respective positions within the left atrium (not shown) and the right subclavian artery 44 via one or more sutures 60 or one or more anastomotic connectors. As such, the pump operatively directs blood from the left atrium (not shown) of the heart 22, through the inflow and outflow cannulae 52, 56, and into the right subclavian artery 44 to improve the distribution of oxygenated blood throughout the patient 20.

To power the implantable device 12, a cable 62 is removably connected to the implantable device 12 via the implantable connector assembly 14 within the patient 20. The cable 62 may extend transdermally from the implantable device 12 to a position in the abdomen where the cable 62 exits the patient 20 and connects to a power supply source (not shown). Suitable power supplies may be any universal-type power supply that sends electrical power to the implantable device 12 through the cable 62 and the implantable connector assembly 14.

Figure 2A:
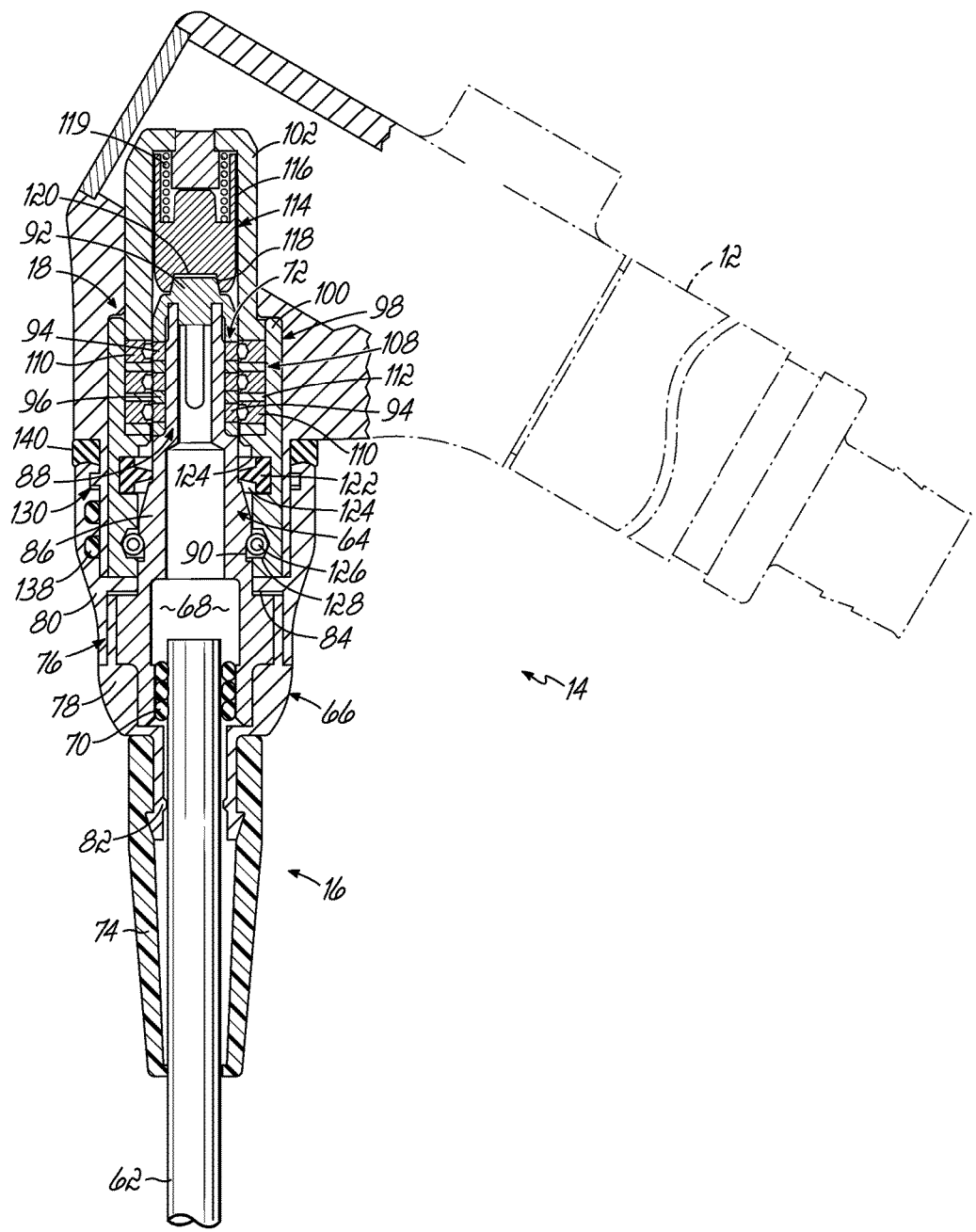
FIG. 2A is a cross-sectional view of the implantable connector assembly of the apparatus shown in FIG. 1.
Figure 2B:
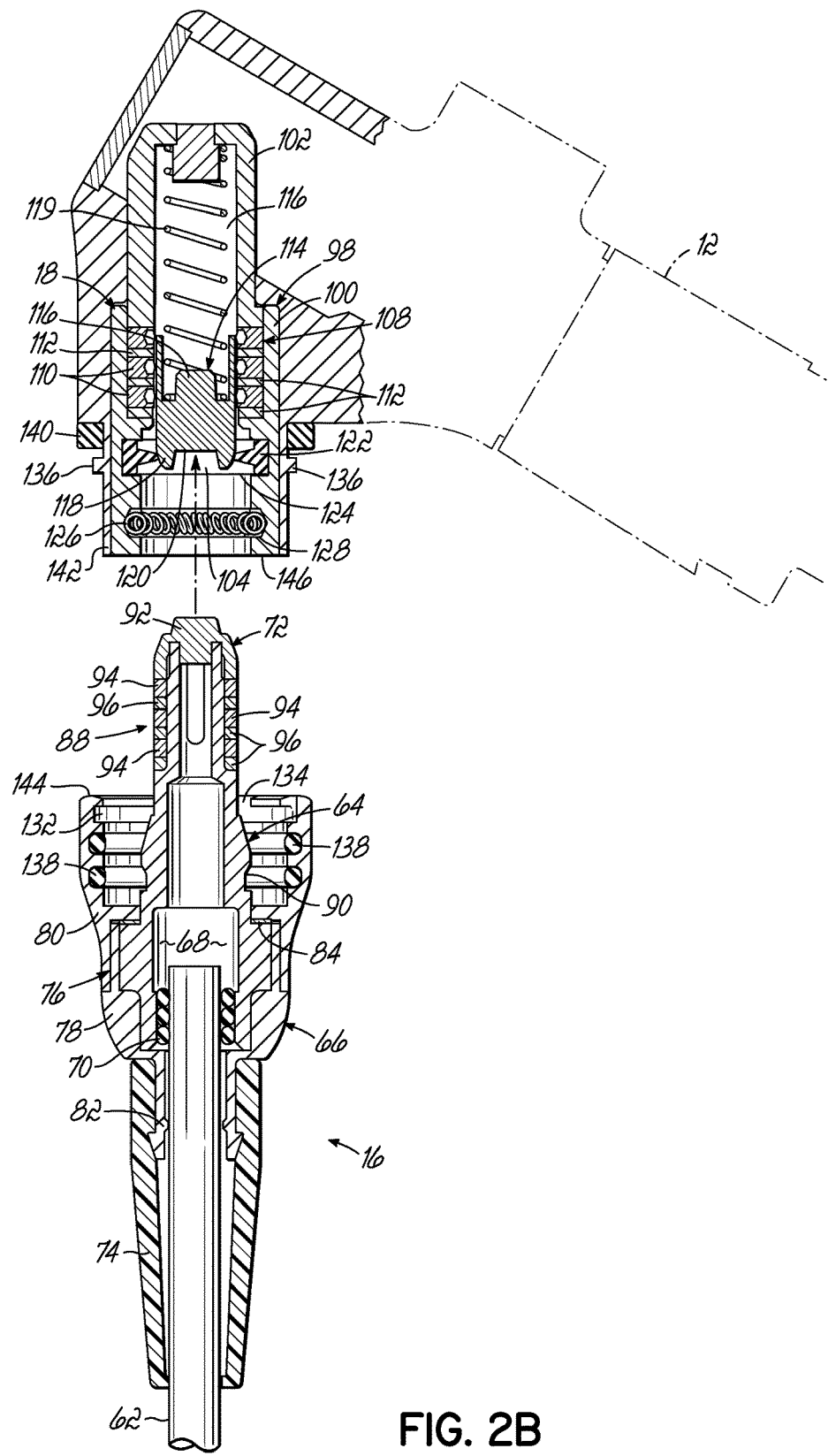
FIG. 2B is similar to FIG. 2A, but shows the implantable connector assembly decoupled.

FIG. 2A and FIG. 2B show the implantable connector assembly 14 having the plug 16 and the receptacle 18 in greater detail. The plug 16 connects to the cable 62 defining a generally flexible electrical conduit (not shown) for communicating the electrical power to the plug 16, whereas the receptacle 18 integrates directly into the implantable device 12. As such, the exemplary embodiment of the implantable connector assembly 14 removably connects the plug 16 directly into the receptacle 18 within the implantable device 12. However, it will be appreciated that the plug 16 and the receptacle 18 may be reversed such that the plug 16 is integrated into the implantable device 12 and the receptacle 18 is connected to the cable 62. It will be further appreciated that either the receptacle 18, or alternatively the plug 16, need not be directly integrated into the implantable device 12. For example, the receptacle 18, or alternatively the plug 16, may directly connect to another cable (not shown) that, in turn, connects to the implantable device 12.

The plug 16 generally includes a plunger body 64 projecting from the cable 62 and a plug housing 66 at least partially surrounding the cable 62 and the plunger body 64. The cable 62 inserts into a space 68 defined within the plunger body 64, and a plurality of cable seals 70, such as o-rings, are positioned on the cable 62 and against the plunger body 64 to inhibit a contaminant from passing between a surrounding environment and the space 68. The space 68 receives electrical wires (not shown) from within the cable 62 for connection to a plug communication structure 72 described below in greater detail.

The plug housing 66 includes a cable cover 74 and an outer plug body 76, each of which is generally hollow for receiving the cable 62 and the plunger body 64. In addition, the outer plug body 76 has a base component 78 and a coupling component 80. The plunger body 64 is rigidly secured within the base component 78 and projects outward from the cable 62 toward the receptacle 18. The base component 78 secures the coupling component 80 in a position proximate to the plunger body 64 and includes a barbed portion 82 securing the cable cover 74 to the cable 62. The base component 78 may be either rigidly or rotatably attached to the coupling component 80. A housing seal 84 is shown in the exemplary embodiment between the base and coupling component 78, 80 to inhibit contamination from passing therebetween.

The plunger body 64 includes a raised portion 86 extending toward an end portion 88. The raised portion 86 defines an annular groove 90 that generally circumscribes the plunger body 64. More particularly, the annular groove 90 and raised portion 86 are annularly surrounded by the coupling component 80, whereas the end portion 88 projects beyond the coupling component 80 toward the receptacle 18. Also, the end portion 88 has a tapered plunger end 92 and the plug communication structure 72. The plunger end 92 opens the receptacle 18 when inserting the plunger body 64 therein such that the plug communication structure 72 may communicate electrical power to the receptacle 18.

According to the exemplary embodiment shown in FIG. 2A and FIG. 2B, the plug communication structure 72 includes a plurality of annular inner electrical conduits 94 electrically isolated from each other by an inner insulator portion 96 of the plunger body 64. The inner electrical conduits 94 receive electrical power from operatively connected electrical wires (not shown), but described briefly above. By way of example, the plug communication structure 72 includes at least two inner electrical conduits 94 and as many as seven inner electrical conduits 94. Alternatively, the plug communication structure 72 includes at least three inner electrical conduits 94 and as many as five inner electrical conduits 94. The plug communication structure 72 may have an outer surface with more than 50% being the inner insulator portion 96 and, more particularly, between 70% and 90% being the inner insulator portion 96 relative to the plurality of inner electrical conduits 94.

The receptacle 18 is configured to removably receive the plug 16 for communicating the electrical power from the plug 16 to the implantable device 12. The receptacle 18 includes a sleeve 98 generally comprised of a coupling tube 100 and an inner tube 102. The inner tube 102 is inserted into the coupling tube 100 and projects outward from the coupling tube 100 toward the implantable device 12. Accordingly, the coupling tube 100 defines an opening 104, and the inner tube 102 defines a bore 106. The inner tube 102 is sized for receiving the end portion 88 of the plunger body 64, while the coupling tube 100 is sized for receiving the raised portion 86 of the plunger body 64. Thus, the opening 104 connects to the bore 106 for receiving the plunger body 64 of the plug 16 within the sleeve 98 of the receptacle 18.

The inner tube 102 also includes a receptacle communication structure 108 configured to cooperate with the plug communication structure 72 for communicating the element, such as the electrical power, therebetween. According to an exemplary embodiment, the receptacle communication structure 108 includes a plurality of annular outer electrical conduits 110 electrically isolated from each other by an outer insulator portion 112 of the inner tube 102. The outer electrical conduits 110 are sized to receive and contact the inner electrical conduits 94 therein for communicating electrical power. The outer electrical conduits 110 are connected to electrical wires (not shown) within the implantable device 12 for delivering electrical power to the remainder of the implantable device 12, such as the pump described above. By way of example, the receptacle communication structure 108 includes at least two outer electrical conduits 110 and as many as seven outer electrical conduits 110. Alternatively, the receptacle communication structure 108 includes at least three outer electrical conduits 110 and as many as five outer electrical conduits 110.

Furthermore, the receptacle 18 includes a resiliently mounted stopper 114 for fluidly sealing the opening 104 and, in turn, inhibiting contamination from entering the bore 106 when the plug 16 is withdrawn from the receptacle 18. The stopper 114 has a recessed end 116 opposite from a sealing end 118. A spring 119 is mounted within the bore 106 and rests within the recessed end 116. Accordingly, the stopper 114 is biased toward the opening 104 to seal the opening 104 with the sealing end 118 when the plug 16 is withdrawn. The sealing end 118 also includes a detent 120 sized for receiving the plunger end 92 when the plunger body 64 is inserted into the sleeve 98 for improved longitudinal and coaxial alignment between stopper 114, the bore 106, and the plunger body 64.

To further fluidly seal the opening 104 and inhibit contamination, the receptacle 18 also includes an annular wiper seal 122 positioned proximate to the opening 104. More particularly, the coupling tube 100 includes an inner seal groove 124 that receives the wiper seal 122 for affixing the wiper seal 122 within the opening 104. The stopper 114, being biased toward the opening 104, contacts the wiper seal 122 with sufficient force to fluidly seal the sealing end 118 of the stopper 114 against the wiper seal 122. As will be described below in greater detail, the wiper seal 122 is also sized to fluidly seal against the end portion 88 of the plunger body 64. Accordingly, the wiper seal 122 further inhibits contamination from entering the opening 104 and bore 106 even when the stopper 114 is displaced longitudinally within the bore 106 by the plunger body 64.

In addition, the coupling tube 100 includes a holding member 126 and an inner holding groove 128. The inner holding groove 128 is annular and extends within the coupling tube 100. The holding member 126 is positioned within the inner holding groove 128 and is sized to engage the annular groove 90 of the plunger body 64 when the plunger body 64 is inserted into the sleeve 98. As shown in the exemplary embodiment of FIG. 2A and FIG. 2B, the holding member 126 is in the form of a toroidal spring that releasably engages the annular groove 90 with enough biasing force to overcome the force of the spring 119 within the bore 106. Thus, the holding member 126 engages the annular groove 90 with sufficient force to hold the plug 16 in a releasably fixed position relative to the receptacle 18. However, it will be appreciated that the holding member 126 may be any annular component sized for the inner holding groove 128 that provides sufficient biasing force for engaging the annular groove 90. For example, a resilient o-ring (not shown) may provide sufficient biasing force for engaging the annular groove 90.

The implantable connector assembly 14 also includes a locking mechanism 130 for locking and unlocking the position of the plug 16 relative to the receptacle 18 for improved sealing therebetween. The locking mechanism 130 has an annular locking channel 132 circumscribed within the coupling component 80 and a plurality of slots 134 through the coupling component 80 to access the plurality of slots 134. The locking mechanism 130 also includes a plurality of tabs 136 proximate to the sleeve 98 and projecting outward from the receptacle 18 generally perpendicular to the longitudinal direction along the sleeve 98. The plurality of tabs 136 and the annular locking channel 132 cooperate such that each tab 136 inserts into the annular locking channel 132 through one of the respective slots 134. The coupling component 80 is then rotated, such as a ¼ turn rotation, to engage the plurality of tabs 136 within the annular locking channel 132 and lock the position of the plug 16 relative to the receptacle 18. Of course, the coupling component 80 may be turned back, such as the ¼ turn, to unlock the position of the plug 16 relative to the receptacle 18.

In the locked position, the coupling component 80 also seals against the receptacle 18 to further inhibit contamination of the plug and receptacle communication structures 72, 108 via a plurality of coupling seals 138 and an outer seal 140. The plurality of coupling seals 138 are positioned within the coupling component 80 and compress against a sidewall 142 in the locked position to inhibit contamination from traveling longitudinally along the implantable connector assembly 14. In contrast, the outer seal 140 sandwiches between a plug end face 144 and a receptacle end face 146 in the locked position to inhibit contamination from traveling radially into the implantable connector assembly 14.

In use, the receptacle 18 and implantable device 12 are implanted at least subcutaneously within the patient 20 (see FIG. 1) without the plug 16 and the remainder of the cable 62 connected to the receptacle 18. The stopper 114 fluidly seals against the wiper seal 122 to inhibit contamination from entering the opening 104 and contaminating the receptacle communication structure 108 within the bore 106. Once implanted, the plunger body 64 of the plug 16 is inserted into the sleeve 98 until the plug communication structure 72 and the receptacle communication structure 108 align, contact, and operatively connect for communication of the element therebetween.

As the plunger body 64 is inserted into the sleeve 98, the plunger end 92 coaxially aligns with the detent 120 and the bore 106. The plunger end 92 displaces the stopper 114 longitudinally along the bore 106 and compresses the spring 119 such that the stopper 114 is no longer fluidly sealed against the wiper seal 122. However, as the wiper seal 122 fails to fluidly seal against the stopper 114, the wiper seal 122 fluidly seals against the end portion 88 of the plunger body 64 passing through the opening 104. In this respect, a fluid seal is generally maintained between the patient 20 and receptacle communication structure 108 during the insertion of the plug 16. The wiper seal 122 also tends to reduce contamination on the plunger body 64 and, in particular, the plug communication structure 72, by wiping contamination from the plunger body 64 during insertion of the plug 16.

Once the plug and receptacle communication structures 72, 108 are properly aligned relative to each other, the holding member 126 engages the annular groove 90 in the plug 16. The engagement of the holding member 126 overcomes the biasing spring 119 to removably hold the plug 16 in position relative to the receptacle 18. To further seal and lock the implantable connector assembly 14, the annular locking channel 132 cooperates with the plurality of tabs 136 by rotating the coupling component 80 relative to the tabs 136. Each tab 136 engages the coupling component 80 within the annular locking channel 132 to lock the plug 16 against the receptacle 18. In addition, the engagement of the coupling component 80 further fluidly seals the implantable connector assembly 14 from contamination longitudinally with the coupling seals 138 and axially with the sandwiched outer seal 140. Finally, the element, such as the electrical power, may be provided to the cable 62 and communicated to the implantable device 12 via the implantable connector assembly 14.

Of course, the implantable connector assembly 14 may be unlocked by returning the rotation of the coupling component 80 described above. The plug 16 is withdrawn from the receptacle 18, and, as such, the stopper 114 again biases against the wiper seal 122 to cover the opening 104 into the bore 106 and fluidly seal the receptacle communication structure 108 from contamination. During the implantation or maintenance of the implantable device 12, it will be appreciated that the insertion and withdrawal of the plug 16 may be repeated as necessary to provide improved access to the patient 20 and reduced surgical complexity (see FIG. 1) by removing the cable 62 from connection with the implantable device 12.

Figure 3A:
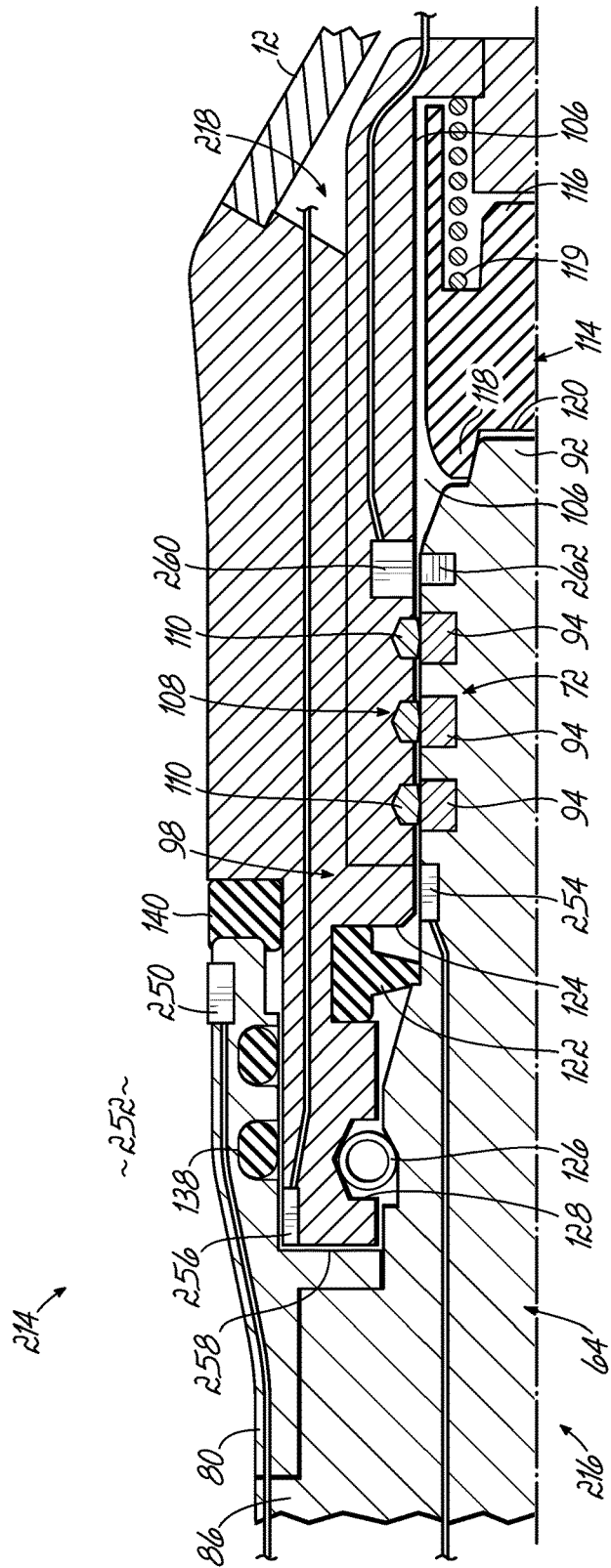
FIG. 3A is an enlarged cross-sectional view taken along a centerline of an alternative embodiment of an implantable connector assembly having a plurality of sensors.

FIG. 3A shows an alternative embodiment of an implantable connector assembly 214 in which like numbers indicate like features described above. According to the alternative embodiment, a plug 216 includes an outer sensor 250 in fluid communication with an unsealed portion 252 of the implantable connector assembly 214, such as the patient 20 (see FIG. 1). In addition, the plug 216 also includes an inner sensor 254 in fluid communication with the fluidly sealed bore 106 proximate to the receptacle communication structure 108. The implantable connector assembly 214 also includes a receptacle 218 having a medial sensor 256 in fluid communication with a gap 258 between coupling seals 138 and the wiper seal 122.

Each of the outer, inner, and medial sensors 250, 254, 256 is operatively driven by a potential voltage via implanted electronics (not shown) monitoring current through the sensors 250, 254, 256. In the event that no current is sensed between the sensors 250, 254, 256, then there is little to effectively no contamination in the gap 258 or in the fluidly sealed bore 106. On the other hand, if a current is sensed in the gap 258, the bore 106, or both the gap 258 and the bore 106, then the presence of current indicates contamination in the gap 258, the bore 106, or the gap 258 and the bore 106. While the exemplary embodiment shown in FIG. 3A shows three sensors 250, 254, 256 for detecting contamination with the applied voltage, it will be appreciated that only two such sensors are needed to sense contamination in either the gap 258 or the bore 106. It will be further appreciated that the sensors may sense conductivity similar to current to achieve another method of detecting contamination. Thus, the invention described herein is not intended to be limited to the three sensors 250, 254, 256 shown in FIG. 3A.

Alternatively, an exemplary embodiment of the implantable connector assembly may only include one or both of the inner sensor 254 or the medial sensor 256 if the inner and medial sensors 254, 256 are in the form of a pH balance sensor or a pressure sensor. For example, only one of the inner or medial sensors 254, 256 is needed to sense a change in the pH balance or pressure. As such, sensing a change in the pH balance or pressure is also indicative of contamination.

In addition, an alignment sensor 260 is positioned on the receptacle 218 within the bore 106, and an alignment component 262 is positioned on the plunger body 64. The alignment sensor 260 is positioned relative to the alignment component 262 such that when the plug and receptacle communication structures 72, 108 operatively connect, the alignment sensor 260 senses the relative alignment with the alignment component 262. In this way, the alignment sensor 260 sensing alignment with the alignment component 262 is indicative of the plug and receptacle communication structures 72, 108 are operatively connected and that the plug 216 is correctly inserted into the receptacle 218. However, the alignment sensor 260 failing to sense the alignment component 262 is indicative of improper alignment between the plug 216 and the receptacle 218. According to an exemplary embodiment, the alignment sensor 260 is a Hall Effect sensor and the alignment component 262 is a magnet. Alternatively, the alignment sensor 260 may be an optical sensor and the alignment component 262 may be a reflective surface. It will be appreciated that one or more of the above sensors 250, 254, 256, 260 and the alignment component 262 may similarly be used alone or in conjunction to detect alignment by sensing current through various circuits of the implanted electronics (not shown). In this way, the sensors 250, 254, 256, 260 and alignment component 262 create redundant sensing to improve the likelihood of detecting a contaminated or improperly aligned connection between the plug 216 and receptacle 218.

In any case, the indication of contamination or indication of improper alignment between the plug 216 and the receptacle 218 may be used to verify a "good connection" between the plug and receptacle communication structures 72, 108 or a "bad connection" between the plug and receptacle communication structures 72, 108. If a "bad connection" is sensed, the implantable device 12 may change operation to accommodate for the contamination until a professional corrects the "bad connection" and/or removes the contamination. For example, the "bad connection" may direct the implantable device 12 to reduce pumping, reduce electric power, or sound an alarm. While the exemplary embodiment shown in FIG. 3A shows the outer and inner sensors 250, 254 on the plug 216 and the medial and alignment sensors 256, 260 on the receptacle 218, it will be appreciated that the sensors 250, 254, 256, 260 may be arranged on either the plug 216 or the receptacle 218 to sense a "good connection" from a "bad connection" as described above.

Figure 3B:
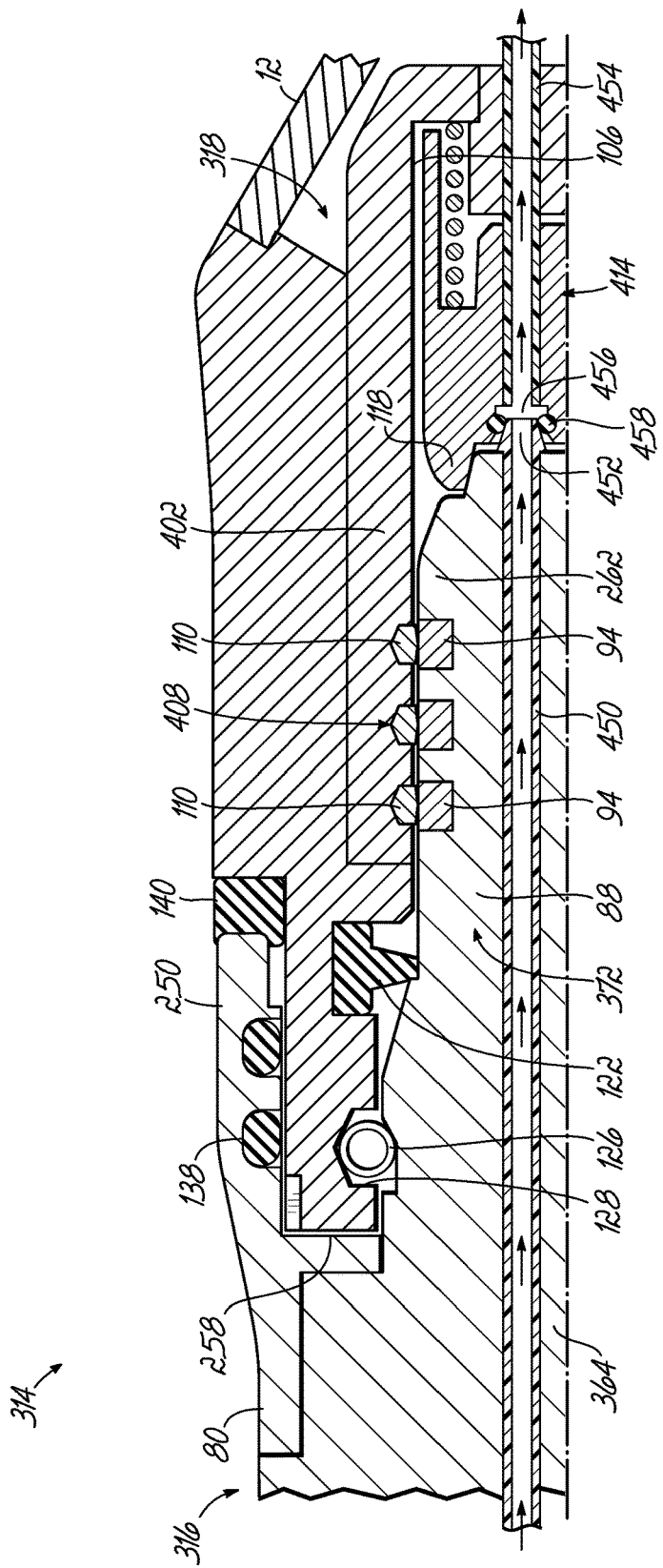
FIG. 3B is an enlarged cross-sectional view taken along a centerline of another alternative embodiment of an implantable connector having a pair of fluid tubes for communicating a fluid.

FIG. 3B shows another alternative embodiment of an implantable connector assembly 314 in which like numbers indicate like features described above. The implantable connector assembly 314 includes a plug communication structure 372 and a receptacle communication structure 408 configured for further communication of a fluid from a plug 316 to a receptacle 318. The plug 316 includes a plunger body 364 in which the plug communication structure 372 also includes a plug fluid tube 450 extending through the plunger body 364 to a cable (not shown) for receiving the fluid. The plug fluid tube 450 has a discharge opening 452 opposite the cable (not shown) that extends beyond the end portion 88 and is configured to discharge the fluid from the discharge opening 452.

The receptacle 318 includes an inner tube 402 in which the receptacle communication structure 408 further includes a receptacle fluid tube 454 extending through the inner tube 402 to the implantable device 12. The receptacle fluid tube 454 further extends through a stopper 414 into a fluid recess 456. Notably, the discharge opening 452 and the fluid recess 456 align as the plug 316 inserts into the receptacle 318. An o-ring 458, or like seal, is positioned within the fluid recess 456. As such, the discharge opening 452 fluidly connects and seals to the fluid recess 456 for communicating fluid from the plug fluid tube 450 and into the receptacle fluid tube 454 for delivery to the implantable device 12.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be from such details without departing from the scope of the general inventive concept.

What is claimed is:

1. An apparatus for implantation within a patient, comprising;
   an implantable device configured for being positioned and operating at least subcutaneously within the patient;
   a cable configured for communicating an element from a source to the implantable device within the patient; and
   an implantable connector assembly for communicating the element from the cable to the implantable device, comprising:
     a plug connected to and surrounding at least a portion of the cable, the plug including a plunger body;
     a receptacle operatively connected to the implantable device, the receptacle including a sleeve and a stopper, the sleeve defining an opening sized for receiving the plunger body, the stopper resiliently mounted within the sleeve and extended in a first configuration toward the opening to cover and fluidly seal the opening for inhibiting contamination from entering within the sleeve when the plunger body is withdrawn from the sleeve; and
     a pair of communication structures positioned respectively on the plunger body and the sleeve, one of the pair of communication structures operatively connecting to the cable for receiving the element from the cable and the other of the pair of communication structures operatively connecting to the implantable device for directing the element to the implantable device, inserting the plunger body into the sleeve displaces the stopper toward a compressed second configuration away from the opening and removably couples the pair of communication structures for communication of the element therebetween; and
     the plug includes a groove, and the receptacle includes a holding member, the groove configured to removably receive the holding member, the holding member overcomes a bias imparted on the plunger in the compressed second configuration to retain the plug within receptacle.

2. The apparatus of claim 1 further comprising:
   a wiper seal positioned proximate to the opening, the stopper fluidly sealing against the wiper seal to further inhibit the entry of contamination within the sleeve.

3. The apparatus of claim 2, wherein the wiper seal fluidly seals against the plunger body during insertion of the plunger body into the sleeve such that the wiper seal removes further contamination from a portion of the plunger body within the sleeve.

4. The apparatus of claim 1, wherein the implantable device is selected from the group consisting of a pump, a pacemaker, a controller, and a battery.

5. The apparatus of claim 1, wherein the receptacle is integrated within the implantable device.

6. The apparatus of claim 1, wherein the plunger body is inserted coaxially within the sleeve.

7. The apparatus of claim 1, wherein the element is an electrical power, and the pair of communication structures are a pair of annular electrical conduits positioned respectively about the plunger body and the sleeve, the pair of annular electrical conduits configured to removably connect for communicating the electrical power therebetween.

8. The apparatus of claim 1, wherein the element is a fluid, and the pair of communication structures are a pair of tubes extending respectively through the plunger body and the sleeve, the pair of tubes configured to removably connect for communicating the fluid therebetween.

9. The apparatus of claim 1 further comprising:
a contamination sensor positioned within the sleeve and operatively connected to one of the plug and the receptacle, wherein the contamination sensor is configured to sense contamination within the sleeve.

10. The apparatus of claim 1 further comprising:
an alignment sensor positioned within the sleeve and operatively connected to one of the plug and the receptacle, wherein the alignment sensor is configured to sense an alignment of the plug relative to the receptacle when the plug mechanically couples to the receptacle.

11. The apparatus of claim 1 wherein the source is a supply source positioned exterior of the patient.

12. An implantable connector assembly for communicating an element from a source exterior of a patient or implanted within the patient to an implantable device within the patient, comprising;
a plug configured to connect to and at least partially surround at least a portion of the source, the plug including a plunger body;
a receptacle configured to connect to the implantable device, the receptacle including a sleeve and a stopper, the sleeve defining an opening sized for receiving the plunger body, the stopper resiliently mounted within the sleeve and extended in a first configuration toward the opening to cover and fluidly seal the opening for inhibiting contamination from entering within the sleeve when the plunger body is withdrawn from the sleeve; and
a pair of communication structures positioned respectively on the plunger body and the sleeve, one of the pair of communication structures is configured to operatively connect to the source for receiving the element from the source and the other of the pair of communication structures is configured to operatively connect to the implantable device for directing the element to the implantable device, wherein inserting the plunger body into the sleeve displaces the stopper toward a compressed second configuration away from the opening and removably couples the pair of communication structures for communication of the element therebetween; and
the plug includes a groove, and the receptacle includes a holding member, the groove configured to removably receive the holding member, the holding member overcomes a bias imparted on the plunger in the compressed second configuration to retain the plug within receptacle.

13. The implantable connector assembly of claim 12 further comprising:
a wiper seal positioned proximate to the opening, the stopper fluidly sealing against the wiper seal to further inhibit the entry of contamination within the Sleeve.

14. The implantable connector assembly of claim 13, wherein the wiper seal fluidly seals against the plunger body during insertion of the plunger body into the sleeve such that the wiper seal removes further contamination from a portion of the plunger body within the sleeve.

15. The implantable connector assembly of claim 12, wherein the plunger body is inserted coaxially within the sleeve.

16. The implantable connector assembly of claim 12, wherein the element is an electrical power, and the pair of communication structures are a pair of annular electrical conduits positioned respectively about the plunger body and the sleeve, the pair of annular electrical conduits configured to removably connect for communicating the electrical power therebetween.

17. The implantable connector assembly of claim 12, wherein the element is a fluid, and the pair of communication structures are a pair of tubes extending respectively through the plunger body and the sleeve, the pair of tubes configured to removably connect for communicating the fluid there between.

18. The implantable connector assembly of claim 12 further comprising:
a contamination sensor positioned within the sleeve and operatively connected to one of the plug and the receptacle, wherein the contamination sensor is configured to sense contamination within the sleeve.

19. The implantable connector assembly of claim 12 further comprising:
an alignment sensor positioned within the sleeve and operatively connected to one of the plug and the receptacle, wherein the alignment sensor is configured to sense an alignment of the plug relative to the receptacle when the plug mechanically couples to the receptacle.

20. A method of communicating an element from a source to an implantable device within the patient, comprising;
inserting a plunger body of a plug into a sleeve of a receptacle, the plug at least partially surrounding at least a portion of the source;
displacing a stopper with the plunger body to unseal an opening within the sleeve;
connecting a communication structure of the plunger body with a communication structure of the sleeve through the opening;
fluidly sealing the plug against the receptacle to inhibit contamination of the communication structures; and
retaining the plug within the receptacle with a holding member disposed within the receptacle and configured to apply a force to the plug to maintain the displacement of the stopper.

21. The method of claim 20 further comprising:
removing the plunger body of the plug from the sleeve of the receptacle and causing;
the stopper to be extended in a first configuration toward the opening to fluidly sealing the opening to further inhibit entry of the contamination into the sleeve.

22. The method of claim 20 wherein the communication structure of the plunger body and the sleeve is an electrical conduit and the method further comprises:
communicating an electrical power from the electrical conduit of the plunger body to the electrical conduit of the sleeve.

23. The method of claim 20 wherein the communication structure of the plunger body and the sleeve is a fluid tube and the method further comprises:
communicating a fluid from the fluid tube of the plunger body to the fluid tube of the sleeve.

24. The method of claim 20 further comprising:
sensing for contamination of the communication structures within at least one of the plug or the receptacle with a contamination sensor.

25. The method of claim 20 further comprising:
sensing alignment between the communication structures of the plug and the receptacle.

26. The method of claim 20 further comprising:
wiping at least a portion of the plunger body with a wiper seal to remove contamination from the portion of the plunger body.

27. The method of claim 20 further comprising:
aligning the plunger body and the sleeve coaxially.

28. The method of claim 20 wherein the source is a supply source exterior of the patient, and the method further comprises:
communicating the element from the supply source exterior of the patient through the communication structures and to the implanted device within the patient.

29. The method of claim 20 wherein the source is another implanted device, and the method further comprises:
communicating the element from one implanted device within the patient through the communication structures and to the other implanted device within the patient.

* * * * *